March 28, 1972 J. H. KLUPENGER Plant Pat. 3,086
AZALEA PLANT
Filed Feb. 13, 1970
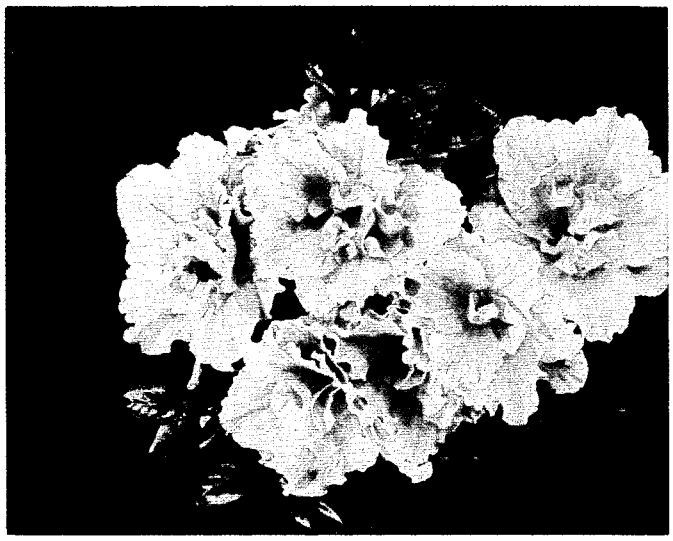
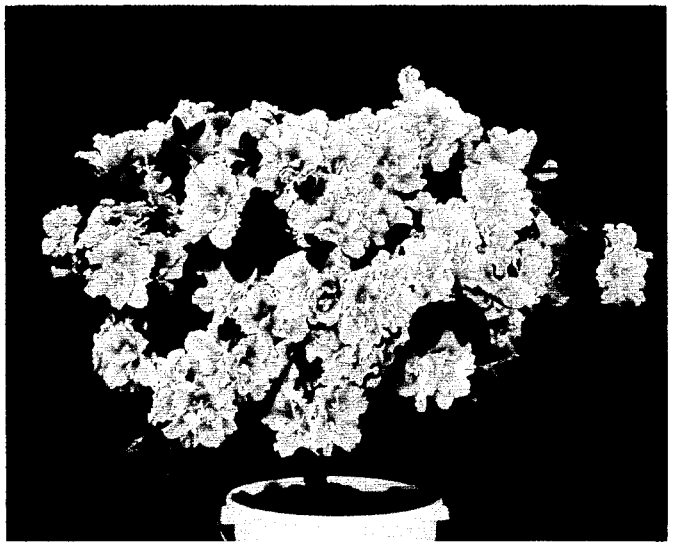
INVENTOR.
JOSEPH H. KLUPENGER
BY Rummler & Snow
Attys.

United States Patent Office

Plant Pat. 3,086
Patented Mar. 28, 1972

3,086
AZALEA PLANT

Joseph H. Klupenger, Aurora, Oreg., assignor to Geo. J. Ball Inc., West Chicago, Ill.

Filed Feb. 13, 1970, Ser. No. 11,360
Int. Cl. A01h *5/00*
U.S. Cl. Plt.—55 1 Claim

ABSTRACT OF THE DISCLOSURE

A new variety of azalea plant having an abundance of variegated light red, pink and white blossoms of medium to large size borne in clusters on an erect and spreading bush of a generally vase-shaped form; the new plant being further distinguished by the long lasting quality of its blossoms, which hold without fading in color until completely past an unusually long blooming season, and by its strong, sturdy and rapid growth to a fully mature, marketable plant in less time than many other azaleas in commercial production.

BACKGROUND OF THE INVENTION

My new variety of azalea plant was discovered in 1962, at Portland Oreg., as a sport of an unnamed seedling resulting from a cross of John Hearron (unpatened) and Chimes (unpatented) produced in the course of breeding efforts carried on by me since 1954 with the object of producing new azalea varieties having better blossom colors, improved flower quality and stronger growth habits. This sport was observed to have outstanding characteristics of blossom size, color and lasting quality and was therefore selected for propagation and trial. Asexual reproduction by cuttings at Portland, Oreg., since 1962 revealed that the new plant not only retained the unusual and very attractive blooming habit of the original sport but also had the additional advantages of a very profuse production of relatively large flowers, a strong and vigorous plant growth habit with good quality of dense foliage, and the ability to reach a fully mature, marketable state in a relatively short time under normal greenhouse procedures.

Continued asexual propagation of this new variety of azalea plant at Portland, Oreg., and then at Aurora, Oreg., has demonstrated that all of its novel characteristics are fixed and hold true from generation to generation and production on a commercial scale is now being carried on at Aurora, Oreg., by means of conventional asexual methods.

DESCRIPTION OF THE DRAWING

My new variety of azalea plant is illustrated in the accompanying full color photographic drawings in which the upper view shows a cluster of the fully opened blooms and the lower figure shows the full blooming plant to illustrate the general form of its growth and its profuse blooming habit.

DESCRIPTION OF THE NEW PLANT

The following is a detailed description of my new variety of azalea plant with color designations according to the R.H.S. Colour Chart edited by the Royal Horticultural Society, London, England.

*The plant*

Origin: Sport.
Parentage: An unnamed seedling cross of "John Hearron" (unpatented) and "Chimes" (unpatented).
Form: Bush—vase shaped.
Height: Average as potted plant—to 3 feet at 5 years.

Growth: Vigorous, strong and spreading with diffused branching.
Foliage:
- *Quantity.*—Abundant and heavy—10 to 15 leaves per stalk or terminal branch.
- *Size of leaf.*—1 to 1¼ inches wide x 2 to 2½ inches long.
- *Shape of leaf.*—Elliptic with acute tip.
- *Texture.*—Smooth, leathery.
- *Aspect.*—Glossy.
- *Color of leaf.*—Upper side—Dark Green 139–A (Green group). Under side—Green 146–B (Yellow Green group).
- *Petioles.*—⅝ inch long.
- *Ribs and veins.*—Average.

*The Bud*

Form: Long and pointed.
Size: 1½ to 1¾ inches long. Diameter: ¾ inch.
Opening: Bud opens slowly.
Color:
- *When sepals first divide.*—White flecks to Pink 62–A (Red-Purple group).
- *When petals begin to unfurl.*—White flecks to Pink 62–A (Red-Purple group).

Peduncle: ⅜" long. Strong and ascending
- *Aspect.*—Hairy.
- *Color.*—White to shades of Light Pink.

*The flower*

Blooming habit: Recurrent. Blooms profusely, once in late spring under normal growing conditions.
Size: Mostly very large—4 inches in diameter, 1 inch deep.
Borne: In clusters.
Shape: Flat when bloom first opens. Form does not change.
Petalage:
- *Number of petals.*—10.
- *Arrangement.*—Imbricated.
- *Form.*—Hose and Hose.
- *Color.*—Outer petals—generally Pink 62–A (Red-Purple group) blending to White, with base of Purple Red 61–A (Ped-Purple group). Inside petal—Generally Red 61–B with longitudinal streaks of Pink 62–A and Red 61–B fading to White at outer edges. Reverse side—Pink 62–A fading to White at margins.
- *Petaloids.*—8 to 10 in number. Size: Average—1½ x ¾ inches. Color: Pink 62–A, blending to White outer edge.
- *Texture.*—Leathery.
- *Appearance.*—Satiny.
- *Discoloration.*—None.

Peduncle: ⅜ inch long. Sturdy and ascending.
Fragrance: None.
Lasting quality: Very good on plant.
Effect of weather: Average for azaleas.
Persistence: Flowers hang on and dry.
Disease resistance: Plant shows no signs of disease since discovery and as group in Portland and Aurora, Oreg.

*Reproductive organs*

Stamens:
- *Anthers.*—1 to 3 in number.
- *Filaments.*—Average 1⅛ inches in length. Color: Yellow 162–A (Greyed-Yellow group).

Pollen: Color—Yellow.
Pistils: One—⅞ inch long.
Stigmas: Color—Yellow 162–A.
Ovaries: Superior—White pubescence.

My new variety of azalea plant most nearly resembles *Petrica superba* (unpatented) in its flower form and its very large flower, with its many petals, is of the Indicum type. The primary distinctiveness of the new variety, however, resides in the variegated coloring of the flower petals which are of a bright red color at the base or flower center with the coloring streaked outwardly in a generally radial direction from the flower center and blending through a lovely pink to a blend of white and pink at the petal margins. The flowers have a very long-lasting quality and hold on the plant for an extraordinary period of time during the blooming period without fading, merely drying on the plant when the blooming season has completely passed. The new plant grows vigorously, strong and sturdy, to a fully mature, marketable plant in less time than is required by many other commercially produced varieties. Also, as a plant for greenhouse forcing, my new variety of azalea has a long holding quality of both flower buds and foliage for late season blooming.

I claim:

1. A new and distinct variety of azalea plant substantially as herein shown and described, characterized by its variegated blossoms having a light red coloring blending in radial streaks through deep pink to white at the petal edges, by its relatively large, many petalled and long-lasting flowers which bloom profusely over the entire plant and hang on to dry on the plant only when the blooming season has completely passed, and by its vigorous growing habit and abundant production of dense foliage.

No references cited.

ROBERT E. BAGWILL, Primary Examiner